US006706912B2

(12) United States Patent
Drent et al.

(10) Patent No.: US 6,706,912 B2
(45) Date of Patent: Mar. 16, 2004

(54) PROCESS FOR THE CARBONYLATION OF ETHYLENICALLY UNSATURATED COMPOUNDS

(75) Inventors: Eit Drent, Amsterdam (NL); Willem Wabe Jager, Amsterdam (NL)

(73) Assignee: Shell Oil Company, Houston, TX (US)

( * ) Notice: Subject to any disclaimer, the term of this patent is extended or adjusted under 35 U.S.C. 154(b) by 129 days.

(21) Appl. No.: 09/805,592

(22) Filed: Mar. 13, 2001

(65) Prior Publication Data

US 2001/0044556 A1 Nov. 22, 2001

(30) Foreign Application Priority Data

Mar. 14, 2000 (EP) ............................................. 00200927
Nov. 1, 2000 (EP) ............................................. 00309654

(51) Int. Cl.⁷ ........................ C07C 67/38; C07C 67/36; C07C 51/10; C07C 51/14
(52) U.S. Cl. ...................... 560/233; 560/204; 560/232; 562/517; 562/522
(58) Field of Search ................................ 560/204, 232, 560/233; 562/519, 522

(56) References Cited

U.S. PATENT DOCUMENTS

| | | | |
|---|---|---|---|
| 4,298,546 A | 11/1981 | McGill | 260/465.9 |
| 4,950,778 A | 8/1990 | Burke et al. | 558/353 |
| 5,434,290 A | 7/1995 | Stahl et al. | 558/353 |
| 5,679,831 A | 10/1997 | Sielcken | 560/204 |
| 5,693,851 A | 12/1997 | Sielcken et al. | 560/207 |
| 5,821,378 A | 10/1998 | Foo et al. | 558/338 |
| 6,018,081 A | 1/2000 | Burke et al. | 568/451 |
| 6,156,934 A | 12/2000 | Suykerbuyk et al. | 568/12 |

FOREIGN PATENT DOCUMENTS

| | | | |
|---|---|---|---|
| DE | 198 40 253 A1 | 3/2000 | C07F/9/50 |
| EP | 0227160 A2 | 7/1987 | C07C/51/14 |
| EP | 0495547 A2 | 7/1992 | C07C/51/14 |
| EP | 0495548 A2 | 7/1992 | C07C/51/14 |
| EP | 0662467 A1 | 7/1995 | C07C/67/38 |
| EP | 0729943 A2 | 9/1996 | C07D/201/08 |
| WO | WO 96/19434 | 12/1995 | C07C/67/38 |
| WO | WO 98/37063 | 2/1998 | C07D/201/08 |
| WO | WO 98/42717 | 10/1998 | C07F/9/6568 |

OTHER PUBLICATIONS

U.S. patent application Ser. No. 09/804,891, filed Mar. 13, 2001.

*Primary Examiner*—Porfirio Nazario-Gonzalez
*Assistant Examiner*—Paul A. Zucker

(57) ABSTRACT

Process for the carbonylation of ethylenically unsaturated compounds having 3 or more carbon atoms by reaction with carbon monoxide and an hydroxyl group containing compound in the presence of a catalyst system. The catalyst system includes (a) a source of palladium cations;
(b) a bidentate diphosphine of formula I,

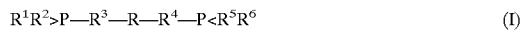

$R^1R^2 > P—R^3—R—R^4—P < R^5R^6$      (I)

wherein P represents a phosphorus atom; $R^1$, $R^2$, $R^5$ and $R^6$ independently represent the same or different optionally substituted organic groups containing a tertiary carbon atom through which the group is linked to the phosphorus atom; $R^3$ and $R^4$ independently represent optionally substituted alkylene groups and R represents an optionally substituted aromatic group;

(c) a source of anions derived from an acid having a pKa less than 3, as measured at 18° C. in an aqueous solution. The process is carried out in the presence of an aprotic solvent.

20 Claims, No Drawings

PROCESS FOR THE CARBONYLATION OF ETHYLENICALLY UNSATURATED COMPOUNDS

BACKGROUND OF THE INVENTION

This invention relates to a process for the carbonylation of ethylenically unsaturated compounds having 3 or more carbon atoms, by reaction with carbon monoxide and a hydroxyl group containing compound in the presence of a catalyst system including a source of palladium cations; a bidentate diphosphine and a source of anions to prepare carboxylic acids and/or esters.

Such a process is known in the art and described in for example EP-A-0495547, EP-A-0495548 and WO-A-9842717.

Depending on the catalyst, reaction conditions and substrates, carbonylation of ethylenically unsaturated compounds having 3 or more carbon atoms can proceed with varying selectivities to the several possible isomeric products in varying yields. Generally only one isomeric product is preferred. The selectivity towards one of several possible isomeric products is called regioselectivity. For the carbonylation of ethylenically unsaturated compounds having 3 or more carbon atoms, regioselectivity towards a linear product, i.e. towards reaction at the primary carbon atom, is often desirable. For example, in the preparation of components of detergent compositions, efforts have been made to increase the selectivity with respect to linear carbonylation products.

Although good selectivities towards a linear product can be obtained by the processes described in EP-A-0495547, EP-A-0495548 and WO-A-9842717, there still exists a need for further improvement of the selectivity towards a linear product.

In WO-A-9619434 a process for the carbonylation of ethylene is described. The process is carried out in the presence of a catalyst system comprising palladium as a preferred Group VIII metal, and a bidentate diphosphine of formula I,

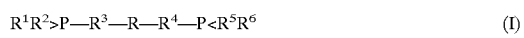

wherein P represents a phosphorus atom; $R^1$, $R^2$, $R^5$ and $R^6$ can independently represent the same or different optionally substituted organic groups containing a tertiary carbon atom through which the group is linked to the phosphorus atom; $R^3$ and $R^4$ independently represent optionally substituted lower alkylene groups and R represents an optionally substituted aromatic group.

In WO-A-9619434 it is mentioned that propene was found to be difficult to carbonylate to the extent that the described catalyst system can be viewed as not being able to carbonylate propene.

SUMMARY OF THE INVENTION

A process for the carbonylation of ethylenically unsaturated compounds having 3 or more carbon atoms is provided, comprising reacting carbon monoxide and a hydroxyl group containing compound in the presence of a catalyst system comprising:

(a) a source of palladium cations;
(b) a bidentate diphosphine of formula I,

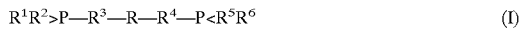

wherein P represents a phosphorus atom; $R^1$, $R^2$, $R^5$ and $R^6$ independently represent the same or different optionally substituted organic groups containing a tertiary carbon atom through which the group is linked to the phosphorus atom; $R^3$ and $R^4$ independently represent optionally substituted alkylene groups and R represents an optionally substituted aromatic group;

(c) a source of anions derived from an acid having a pKa less than 3, as measured at 18° C. in an aqueous solution; in the presence of an aprotic solvent.

DETAILED DESCRIPTION OF THE INVENTION

It has now surprisingly been found that a catalyst system as described in WO-A-9619434 can be successful in the carbonylation of ethylenically unsaturated compounds having 3 or more carbon atoms, when the carbonylation process is carried out in the presence of an aprotic solvent. Moreover, carbonylation in the presence of this specific catalyst system and environment results in a high regioselectivity towards a linear product.

Accordingly, this invention provides a process for the carbonylation of ethylenically unsaturated compounds having 3 or more carbon atoms by reaction with carbon monoxide and a hydroxyl group containing compound in the presence of a catalyst system including:

(a) a source of palladium cations;
(b) a bidentate diphosphine of formula I,

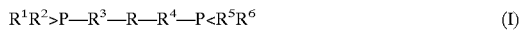

wherein P represents a phosphorus atom; $R^1$, $R^2$, $R^5$ and $R^6$ independently represent the same or different optionally substituted organic groups containing a tertiary carbon atom through which the group is linked to the phosphorus atom; $R^3$ and $R^4$ independently represent optionally substituted alkylene groups and R represents an optionally substituted aromatic group;

(c) a source of anions derived from an acid having a pKa less than 3, as measured at 18° C. in an aqueous solution; carried out in the presence of an aprotic solvent.

In the process according to the invention, suitable sources for palladium of component (a) include its salts, such as for example the salts of palladium and halide acids, nitric acid, sulphuric acid or sulphonic acids; palladium complexes, e.g. with carbon monoxide or acetylacetonate, or palladium combined with a solid material such as an ion exchanger. Preferably, a salt of palladium and a carboxylic acid is used, suitably a carboxylic acid with up to 12 carbon atoms, such as salts of acetic acid, propionic acid and butanoic acid, or salts of substituted carboxylic acids such as trichloroacetic acid and trifluoroacetic acid. A very suitable source is palladium(II) acetate.

In the diphosphine of formula I, R represents an optionally substituted aromatic group which is linked to the phosphorus atoms via the alkylene groups. The aromatic group can be a monocyclic group, such as for example a phenyl group or a polycyclic group, such as for example naphtyl, anthryl or indyl group. Preferably, the aromatic group R contains only carbon atoms, but R can also represent an aromatic group wherein a carbon chain is interrupted by one or more hetero atoms, such as nitrogen, sulphur or oxygen atom in for example a pyridine, pyrrole, furan, thiophene, oxazole or thiazole group. Most preferably the aromatic group R represents a phenyl group.

Optionally the aromatic group is substituted. Suitable substituents include groups containing hetero-atoms such as halides, sulphur, phosphorus, oxygen and nitrogen. Examples of such groups include chloride, bromide, iodide and groups of the general formula —O—H, —O—$X^2$, —CO—$X^2$, —CO—O—$X^2$, —S—H, —S—$X^2$, —CO—S—$X^2$, —$NH_2$, —$NHX^2$, —$NR^2X^3$, —$NO_2$, —CN, —CO—$NH_2$, —CO—$NHX^2$, —CO—$NX^2X^3$ and —$CI_3$ in which $X^2$ and $X^3$, independently, represent alkyl groups having from 1 to 4 carbon atoms like methyl, ethyl, propyl, isopropyl and n-butyl.

If the aromatic group is substituted it is preferably substituted with one or more aryl, alkyl or cycloalkyl groups, preferably having from 1 to 10 carbon atoms. Suitable groups include, methyl, ethyl, propyl, iso-propyl, butyl and iso-butyl, phenyl and cyclohexyl.

Most preferably, however, the aromatic group is non-substituted and only linked to the alkylene groups which connect it with the phosphorus atoms. Preferably the alkylene groups are connected at adjacent positions, for example the 1 and 2 positions, of the aromatic group.

Preferably the alkylene groups $R^3$ and $R^4$ are lower alkylene groups. By lower alkylene groups is understood alkylene groups comprising from 1 to 4 carbon atoms. The alkylene groups can be substituted, for example with alkyl groups, or non-substituted. Preferably the alkylene groups are non-substituted. More preferably the alkylene groups are unsubstituted methylene or ethylene groups, most preferably methylene groups.

$R^1$, $R^2$, $R^5$ and $R^6$ can independently represent organic groups containing a tertiary carbon atom through which the group is linked to the phosphorus atom. The groups $R^1$, $R^2$, $R^5$ and $R^6$ are only connected to each other via the phosphorus atom. The organic groups preferably have from 4 to 20 carbon atoms and more preferably from 4 to 8 carbon atoms. The tertiary carbon atom can be substituted with aliphatic, cyclo-aliphatic or aromatic substituents or can form part of a substituted saturated or non-saturated aliphatic ring structure. Hence examples of suitable organic groups are tert-butyl, 2-(2-methyl)-butyl, 2-(2-ethyl)butyl, 2-(2-phenyl)butyl, 2-(2-methyl)pentyl, 2-(2-ethyl)pentyl, 2-(2-methyl-4-phenyl)-pentyl and 1-(1-methyl)cyclohexyl groups. Preferably the tertiary carbon atom is substituted with alkyl groups, i.e. preferably the organic group is a tertiary alkyl group. Of these, tert-butyl groups are most preferred. Preferably the groups $R^1$, $R^2$, $R^5$ and $R^6$ represent the same tertiary alkyl groups, most preferably groups $R^1$, $R^2$, $R^5$ and $R^6$ are tert-butyl groups.

An especially preferred bidentate diphosphine is 1,2-bis[(di(tert-butyl)phospinomethyl]benzene (also known as bis[di(tert-butyl)phospino]-o-xylene).

The ratio of moles of bidentate diphosphine, i.e. catalyst component (b), per mole atom of palladium cations, i.e. catalyst component (a), ranges from 0.5 to 10, preferably from 1 to 3.

The source of anions derived from acid having a pKa below 3.0 (measured in aqueous solution at 18° C.) preferably is a non-coordinating anion. Hereby is meant that little or no covalent interaction takes place between the palladium and the anion.

Examples of suitable anions include anions of phosphoric acid, sulphuric acid, sulphonic acids and halogenated carboxylic acids such as trifluoroacetic acid.

Sulphonic acids are in particular preferred, for example trifluoromethanesulphonic acid, p-toluene-sulphonic acid and 2,4,6-trimethylbenzene sulphonic acid, 2-hydroxypropane-2-sulphonic acid, tert-butyl sulphonic acid, methyl sulphonic acid. The acid can also be an ion exchanging resin containing sulphonic acid groups. Especially preferred are methyl sulphonic acid, tert-butyl sulphonic acid and 2,4,6-trimethylbenzene sulphonic acid.

The molar ratio of the source of anions and palladium is preferably between 1:1 and 10:1 and more preferably between 1:1 and 5:1.

The process is carried out in the presence of an aprotic solvent. Suitable solvents include ketones, such as for example methylbutylketone; ethers, such as for example anisole (methyl phenyl ether), 2,5,8-trioxanonane (diglyme), diethylether, tetrahydrofuran, diphenylether, diisopropylether and the dimethylether of di-ethylene-glycol; esters, such as for example methylacetaat, dimethyladipate and butyrolactone; amides, such as for example dimethylacetamide and N-methylpyrrolidone; and sulfoxides and sulphones, such as for example dimethylsulphoxide, di-isopropylsulphone, sulfolane (tetrahydrothiophene-2,2-dioxide) 2-methylsulfolane and 2-methyl-4-ethylsulfolane.

Very suitable are aprotic solvents having a dielectric constant that is below a value of 50, more preferably in the range of about 3 to about 8, at 298.15 K and 1 bar. In the present context, the dielectric constant for a given solvent is used in its normal meaning of representing the ratio of the capacity of a condenser with that substance as dielectric to the capacity of the same condenser with a vacuum for dielectric. Values for the dielectric constants of common organic liquids can be found in general reference books, such as the Handbook of Chemistry and Physics, $76^{th}$ edition, edited by David R. Lide et.al, and published by CRC press in 1995, and are usually quoted for a temperature of about 20 or 25° C., i.e. about 293.15 or 298.15 K, and atmospheric pressure, i.e. about 1 bar, or can readily be converted to that temperature and pressure using the conversion factors quoted. If no literature data for a particular compound is available, the dielectric constant may be readily measured using established physico-chemical methods.

For example, the dielectric constant of anisole is 4.3 (at 294.2 K), of diethyl ether is 4.3 (at 293.2 K), of sulfolane is 43.4 (at 303.2 K), of methylpentanoate is 5.0 (at 293.2 K), of diphenylether is 3.7 (at 283.2 K), of dimethyladipate is 6.8 (at 293.2 K), of tetrahydrofuran is 7.5 (at 295.2 K), of methylnonanoate is 3.9 (at 293.2 K). A preferred solvent is anisole.

If the hydroxyl group containing compound is an alkanol, a further preferred aprotic solvent is the ester carbonylation product of the ethylenically unsaturated compound, carbon monoxide and the alkanol.

The process is advantageously carried out in an excess of aprotic solvent, i.e. at a ratio (v/v) of aprotic solvent to hydroxyl group containing compound of at least 1:1. Preferably this ratio ranges from 1:1 to 10:1 and more preferably from 1:1 to 5:1. Most preferably the ratio (v/v) ranges from 1.5:1 to 3:1.

The ethylenically unsaturated compound has at least 3 carbon atoms in an unsaturated carbon chain. Preferably the ethylenically unsaturated compound has from 4 to 20 and more preferably from 4 to 14 carbon atoms. The ethylenically unsaturated compound is preferably an alkene having 1 to 3 carbon-carbon double bonds per molecule. The alkene can be substituted or non-substituted. Suitable substituents include alkyl and aryl groups as well as groups containing hetero-atoms such as halides, sulphur, phosphorus, oxygen and nitrogen. Examples of substituents include chloride, bromide, iodide and hydroxy, alkoxy, carboxy, amino, amido, nitro, cyano, thiol or thioalkoxy groups.

Examples of ethylenically unsaturated compounds having 3 or more carbon atoms include propene, 1-butene, 2-butene, isobutene, pentenes, hexenes, octenes and dodecenes, 1,5-cyclooctadiene, cyclododecene, methyl pentenoate and pentene nitril.

The process according to the invention has been found to be especially advantageous for the carbonylation of those compounds which are internally unsaturated, such as for example 2-butene or methyl-3-pentenoate. For these compounds side-reactions more easily occur and linear products are more difficult to obtain. With the process of the present invention high regioselectivity towards the linear product can also be obtained for internally unsaturated compounds.

Preferred hydroxyl group containing compounds are water and/or alkanols. If the hydroxyl group containing compound is water, the product obtained will be a carboxylic acid. Esters are obtained if the hydroxyl group containing compound is an alkanol. More preferably the hydroxyl group containing compound is an alkanol. Suitable alkanols include monoalcohols, preferably those having from 1 to 6 carbon atoms per molecule such as for example methanol, ethanol, propanol, isopropanol, butanol and phenol, and poly-alkanols such as 1,2-ethanediol and 1,3-propanediol.

The advantages of the invention are especially clear when an ethylenically unsaturated compound having 3 or more, and more particularly 4 or more, carbon atoms, such as for example octene or dodecene, is reacted with carbon monoxide and an alkanol having 3 or less, more particular 2 or 1 carbon atoms.

The ratio (v/v) of ethylenically unsaturated compound and hydroxyl group containing compound can vary between wide limits and suitably lies in the range of 1:0.1 to 1:10, more suitably from 2:1 to 1:2.

The carbonylation reaction according to the invention is carried out at moderate temperatures and pressures. Suitable reaction temperatures are in the range of about 50–250° C., preferably in the range of about 80–120° C. The reaction pressure is usually at least atmospheric. Suitable pressures are in the range of about 1 to about 100 bar, preferably in the range of about 5 to about 65 bar.

Carbon monoxide partial pressures in the range of about 1–65 bar are preferred. In the process according to the present invention, the carbon monoxide can be used in its pure form or diluted with an inert gas such as nitrogen, carbon dioxide or noble gases such as argon. Small amounts of hydrogen can also be present. In general, the presence of more than about 5% hydrogen is undesirable, since this can cause hydrogenation of the conjugated diene.

The amount of catalyst used in the process is not critical. Good results are obtained when the amount of palladium cations is in the range of about $10^{-7}$ to about $10^{-1}$ gram atom per mole of ethylenically unsaturated compound. Preferably this amount is in the range of about $10^{-5}$ to about $5.10^{-2}$ gat per mole.

The invention will be illustrated by the following non-limiting examples.

EXAMPLES 1–2 AND COMPARATIVE EXAMPLES A–C

The experiments were carried out in a 250 ml magnetically stirred autoclave. The autoclave was charged with 0.25 mmol of palladium(II) acetate, 0.6 mmol of bidentate diphosphine ligand as indicated in Table I, 0.5 mmol acid as indicated in Table I, 30 ml 2-butene and a specific amount of hydroxyl group containing compound and solvent as indicated in Table I. After being flushed with carbon monoxide, the autoclave was pressurized with carbon monoxide to a partial pressure as indicated in Table I. Subsequently, the reactor was sealed and the contents were heated to 100° C. and maintained at that temperature for 3 hours. The initial rate of carbonylation is indicated in Table I. The initial rate of carbonylation is defined as the mean rate of carbon monoxide consumption over the first 30% substrate conversion. After cooling, a sample was taken from the contents of the reactor and analyzed by Gas Liquid Chromatography (GLC). The 2-butene was for nearly 100% converted to esters. The ester product mainly consisted of linear methylpentanoate and branched 2-methyl methylbutanoate. The selectivity towards the linear methylpentanoate is indicated in Table I.

The examples show that the best results are obtained when using 1,2-bis[di(tert-butyl)phospinomethyl]benzene as a ligand. Comparative examples A,B,C show that the use of an alternative ligand, e.g. 1,3-bis[di(tert-butyl)-phospino]propane or 1,3-P,P'-di(2-phospha-1,3,5,7-tetra-methyl-6,9,10-trioxatricyclo [3.3.1.1{3.7}]decyl) propane leads to only moderate product linearity.

TABLE I

Carbonylation of 2-butene

| Ex. | Ligand | Acid | Solvent (ml) | Hydroxyl group containing compound (ml) | CO (bar) | Initial reaction rate | Product linearity (%) |
|---|---|---|---|---|---|---|---|
| 1 | TPB | t-BuS | anisole (40) | methanol (20) | 60 | 290 | 97 |
| 2 | TPB | t-BuS | anisole (40) | methanol (20) | 30 | 330 | 97 |
| A | TPP | t-BuS | anisole (40) | methanol (20) | 30 | 625 | 93 |
| B | DPA3 | t-BuS | none | methanol (40) | 30 | 170 | 82 |
| C | DPA3 | t-BuS | sulfolane (40) | methanol (40) | 30 | 200 | 82 | t-BuS = tert-butyl sulphonic acid
TPB = 1,2-bis[di(tert-butyl)phospinomethyl]benzene
TPP = 1,3-bis[di(tert-butyl)phospino]propane
DPA3 = 1,3-P,P'-di(2-phospha-1,3,5,7-tetramethyl-6,9,10-trioxatricyclo [3.3.1.1{3.7}]-decyl) propane

EXAMPLES 3–5 AND COMPARATIVE EXAMPLES D–F

The experiments were carried out in a 250 ml magnetically stirred autoclave. The autoclave was charged with 0.25 mmol of palladium(II) acetate, 0.6 mmol of bidentate diphosphine ligand as indicated in Table II, a specific amount of acid as indicated in Table II, 20 ml 1-octene and a specific amount of hydroxyl group containing compound and solvent as indicated in Table II. After being flushed, the autoclave was pressurized with carbon monoxide to a partial pressure of 30 bar. Subsequently, the reactor was sealed and the contents were heated to the temperature as indicated in Table II and maintained at that temperature for 3 hours. The initial rate of carbonylation is indicated in Table II. The initial rate of carbonylation is defined as the mean rate of carbon monoxide consumption over the first 30% substrate conversion. After cooling, a sample was taken from the contents of the reactor and analysed by GLC. The octene was for nearly 100% converted to esters. The ester product mainly consisted of methylnonanoate, 2-methyl methyloctanoate and 2-ethyl methylheptanoate. The selectivity towards the linear methylnonanoate is indicated in Table II.

The examples show that the best results are obtained when using 1,2-bis[di(tert-butyl)phosphinomethyl]benzene as a ligand and an ether having a dielectric constant of 4.3 (at 294.2 K), i.e anisole, as a solvent. The use of sulfolane as a solvent also results in a high product selectivity, however, less than for anisole. Comparative examples D, E and F show that the use of an alternative ligand, e.g. 1,3-bis[di(tert-butyl)phospino]propane or 1,3-P,P'-di(2-phospha-1,3,5,7-tetramethyl-6,9,10-trioxatricyclo [3.3.1.1{3.7}]decyl) propane, leads to only moderate product linearity for the esters obtained.

ligand and anisole as a solvent. Comparative examples G-K show that the use of an alternative ligand, e.g. 1,3-bis[di(tert-butyl)phospino]propane or 1,3-P,P'-di(2-phospha-1,3,5,7-tetramethyl-6,9,10-trioxatricyclo [3.3.1.1{3.7}]decyl) propane leads to only moderate product linearity. Remarkably the use of an aprotic solvent in addition to one of the alternative ligands leads to decreased product linearity, whereas the use of an aprotic solvent in combination with the other alternative ligand leads to increased product linearity.

TABLE III

Carbonylation of methyl-3-pentenoate

| Ex. | Ligand | Solvent (ml) | Hydroxyl group containing compound (ml) | CO (bar) | Initial reaction rate | Product linearity (%) |
|---|---|---|---|---|---|---|
| G | TPP | None | methanol (40) | 60 | 20 | 89 |
| H | TPP | anisole (40) | methanol (10) | 60 | 100 | 94 |
| I | DPA3 | none | methanol (40) | 20 | 115 | 84 |
| J | DPA3 | anisole (40) | methanol (10) | 60 | 50 | 70 |
| K | DPA3 | anisole (30) | methanol (20) | 30 | 250 | 80 |
| 6 | TPB | anisole (40) | methanol (10) | 60 | 150 | 96 |

TABLE II

Carbonylation 1-octene

| Ex. | Ligand | Acid (mmol) | Solvent (ml) | Hydroxyl group containing compound (ml) | T (° C.) | Initial reaction rate | Product linearity (%) |
|---|---|---|---|---|---|---|---|
| 3 | TPB | 2,4,6 MBS (0.5) | anisole (40) | methanol (20) | 100 | 70 | 97 |
| 4 | TPB | t-BuS (1) | anisole (40) | methanol (20) | 110 | 100 | 97 |
| 5 | TPB | t-BuS (0.5) | sulfolane (40) | methanol (20) | 100 | 70 | 93 |
| D | TPP | t-BuS (0.5) | anisole (40) | methanol (20) | 100 | 120 | 90 |
| E | TPP | t-BuS (1) | sulfolane (40) | methanol (20) | 100 | 60 | 84 |
| F | DPA3 | t-BuS (0.5) | sulfolane (40) | methanol (20) | 100 | 90 | 82 |

2,4,6 MBS = 2,4,6-trimethyl-benzene sulphonic acid

EXAMPLE 6 AND COMPARATIVE EXAMPLES G–K

The experiments were carried out in a 250 ml magnetically stirred autoclave. The autoclave was charged with 0.25 mmol of palladium(II) acetate, 0.6 mmol of bidentate diphosphine ligand as indicated in Table III, 1 mmol tert-butyl sulphonic acid, 10 ml methyl-3-pentenoate and a specific amount of hydroxyl group containing compound and solvent as indicated in Table III. After being flushed, the autoclave was pressurized with carbon monoxide to a partial pressure as indicated in Table III. Subsequently, the reactor was sealed and the contents were heated to 100° C. and maintained at that temperature for 3 hours. The initial rate of carbonylation is indicated in Table III. The initial rate of carbonylation is defined as the mean rate of carbon monoxide consumption over the first 30% substrate conversion. After cooling, a sample was taken from the contents of the reactor and analysed by GLC. The methyl-3-pentenoate was for nearly 100% converted to diesters. The diester product contained mainly dimethyladipate and 2-methyl dimethylglutarate and a small amount of 2-ethyl dimethylsuccinate. The selectivity towards the linear dimethyladipate is indicated in Table III.

The examples show that the best result is obtained when using 1,2-bis[di(tert-butyl)phospinomethyl]benzene as a

I claim:

1. A process for the carbonylation of ethylenically unsaturated compounds having 3 or more carbon atoms comprising reacting carbon monoxide and at least one hydroxyl group containing compound in the presence of a catalyst system comprising:
   (a) a source of palladium cations;
   (b) a bidentate diphosphine of formula I, $$R^1R^2{>}P{-}R^3{-}R{-}R^4{-}P{<}R^5R^6 \qquad (I)$$

wherein P represents a phosphorus atom; $R^1$, $R^2$, $R^5$ and $R^6$ independently represent the same or different optionally substituted organic groups containing a tertiary carbon atom through which the group is linked to the phosphorus atom, $R^3$ and $R^4$ independently represent optionally substituted alkylene groups and R represents an optionally substituted aromatic group; and (c) a source of anions derived from an acid having a pKa less than 3, as measured at 18° C. in an aqueous solution; in the presence of an aprotic solvent.

2. The process of claim 1 wherein R represents a phenyl group.

3. The process of claim 1 wherein $R^3$ and $R^4$ represents methylene groups.

4. The process of claim 1 wherein $R^1$, $R^2$, $R^5$ and $R^6$ represent tert-butyl groups.

5. The process of claim 1 wherein the source of anions is derived from a sulfonic acid.

6. The process of claim 1 wherein the aprotic solvent has a dielectric constant that is below a value of 50 at 298.15 K and 1 bar.

7. The process of claim 6 wherein the aprotic solvent is anisole.

8. The process of claim 1 wherein the aprotic solvent is an ester carbonylation product of a ethylenically unsaturated compound, carbon monoxide and an alkanol.

9. The process of claim 1 wherein the hydroxyl group containing compound is an alkanol.

10. The process of claim 1 wherein the ethylenically unsaturated compound is internally unsaturated.

11. The process of claim 2 wherein the aprotic solvent has a dielectric constant that is below a value of 50 at 298.15 K and 1 bar.

12. The process of claim 11 wherein the aprotic solvent is anisole.

13. The process of claim 2 wherein the aprotic solvent is an ester carbonylation product of a ethylenically unsaturated compound, carbon monoxide and an alkanol.

14. The process of claim 2 wherein the hydroxyl group containing compound is an alkanol.

15. The process of claim 2 wherein the ethylenically unsaturated compound is internally unsaturated.

16. The process of claim 5 wherein the aprotic solvent has a dielectric constant that is below a value of 50 at 298.15 K and 1 bar.

17. The process of claim 16 wherein the aprotic solvent is anisole.

18. The process of claim 5 wherein the aprotic solvent is an ester carbonylation product of a ethylenically unsaturated compound, carbon monoxide and an alkanol.

19. The process of claim 5 wherein the hydroxyl group containing compound is an alkanol.

20. The process of claim 5 wherein the ethylenically unsaturated compound is internally unsaturated.

* * * * *